(12) United States Patent
Ulhenhaut et al.

(10) Patent No.: US 11,639,907 B2
(45) Date of Patent: May 2, 2023

(54) DEVICE FOR DETERMINING THE DEW POINT OF A GAS IN A PROCESS CHAMBER AND HEAT TREATMENT DEVICE HAVING SUCH A DEVICE FOR DETERMINING THE DEW POINT

(71) Applicant: BELIMED AG, Zug (CH)

(72) Inventors: Dirk Ingmar Ulhenhaut, Zürich (CH); Jochen Ganz, Uster (CH)

(73) Assignee: BELIMED AG, Zug (CH)

( * ) Notice: Subject to any disclaimer, the term of this patent is extended or adjusted under 35 U.S.C. 154(b) by 663 days.

(21) Appl. No.: 16/613,619

(22) PCT Filed: May 31, 2018

(86) PCT No.: PCT/EP2018/064342
§ 371 (c)(1),
(2) Date: Nov. 14, 2019

(87) PCT Pub. No.: WO2018/224388
PCT Pub. Date: Dec. 13, 2018

(65) Prior Publication Data
US 2020/0116659 A1 Apr. 16, 2020

(30) Foreign Application Priority Data

Jun. 7, 2017 (EP) .................................... 17174730

(51) Int. Cl.
*G01N 25/68* (2006.01)
*A61L 2/07* (2006.01)
*A61L 2/28* (2006.01)

(52) U.S. Cl.
CPC ............... *G01N 25/68* (2013.01); *A61L 2/07* (2013.01); *A61L 2/28* (2013.01); *A61L 2202/14* (2013.01); *A61L 2202/24* (2013.01)

(58) Field of Classification Search
CPC .......... A61L 2/07; A61L 2/28; A61L 2202/14; A61L 2202/24; G01N 25/68
See application file for complete search history.

(56) References Cited

U.S. PATENT DOCUMENTS

| 3,396,574 A | 8/1968 | Hanlein et al. |
| 2006/0057021 A1* | 3/2006 | Sawyer ..................... A61L 2/24 422/26 |

FOREIGN PATENT DOCUMENTS

| CH | 438 784 | 12/1967 |
| DE | 1 801 296 | 5/1969 |

(Continued)

OTHER PUBLICATIONS

Machine translation of WO 2011/110197 (Year: 2011).*
(Continued)

*Primary Examiner* — Timothy C Cleveland
(74) *Attorney, Agent, or Firm* — Finch & Maloney PLLC

(57) ABSTRACT

A device (1) for determining the dew point of a gas in a process chamber (2) which comprises a temperature control element (3) and a temperature sensor (4) for determining the temperature in the process chamber (2). The temperature sensor is in a thermally conductive functional connection with the temperature control element (3), and the temperature control element (3) is designed to actively heat and cool the temperature sensor (4). The temperature sensor is arranged in direct contact with the temperature control element (3).

10 Claims, 3 Drawing Sheets

(56) References Cited

FOREIGN PATENT DOCUMENTS

WO    2010/070273  A1    6/2010
WO    2011/110197  A1    9/2011

OTHER PUBLICATIONS

International Search Report Corresponding to PCT/EP2018/064342 dated Jul. 9, 2018.
Written Opinion Corresponding to PCT/EP2018/064342 dated Jul. 9, 2018.

* cited by examiner

DEVICE FOR DETERMINING THE DEW POINT OF A GAS IN A PROCESS CHAMBER AND HEAT TREATMENT DEVICE HAVING SUCH A DEVICE FOR DETERMINING THE DEW POINT

The invention relates to a device for determining the dew point of a gas in a process chamber and, in particular, for determining the steam purity, preferably the presence of non-condensible gases, in a process chamber. The invention further relates to a heat treatment device with a device according to the invention for determining the dew point of a gas in a process chamber.

Such devices are employed in the heat treatment, in particular in the sterilization, of objects that have locations that are difficult for the gas being used to reach, such as is the case, for example, with stacks of hand towels or the ends of capillaries or endoscopes. In sterilization it is assumed that the equilibrium temperature between the gas and liquid phases is reached throughout the entire process chamber. If, however, as described above, difficult-to-reach locations are present, then in some circumstances this steam purity is not reached either locally or globally. As a result, the desired temperature is not reached, or only with a delay, so that the sterilization is designated as unsuccessful.

Different devices are therefore used in order to confirm that a sterilization has been carried out correctly. Sensors are known that change color on reaching the required temperature and in the presence of moisture, and thus confirm that the required temperature has been reached at that location. It is, however, disadvantageous that a check is only possible after the whole process is completed. Color change sensors, furthermore, are also subject to disadvantages in terms of the accuracy and reliability, since the color change depends not only on the temperature, but also on the humidity and on the treatment duration.

Other devices provide for the arrangement of a thermally conductive body in a process chamber. The thermally conductive body is connected to a temperature control device for changing the temperature of the body, and is provided with temperature sensors. Through heating and cooling the body, condensation of the process gas is created at the body itself, wherein the condensation heat that is released causes a discontinuity in the cooling curve of the body. Such a device is known from EP 0 286 834. The cross-sectional area of the body is smaller than the condensation-facilitating surface of the body, so that the temperature of the condensation-facilitating surface is determined by the temperature of the condensate. It is disadvantageous with such an arrangement that it cannot be arbitrarily miniaturized, since the condensation-facilitating surface must always be in a certain relation to the cross-sectional area. In addition, the device must be arranged partially outside the process chamber, which restricts the range of applications of such a device.

It is therefore the object of the invention to provide a device for determining the dew point of a gas that avoids the disadvantages of the known, and in particular enables monitoring of the dew point of a gas practically in real-time, and which at the same time can be miniaturized.

The object is achieved with a device as claimed in the independent claim. The device according to the invention for determining the dew point of a gas in a process chamber comprises a temperature control element and a temperature sensor for determining the temperature in the process chamber, which is in operative, thermally conductive connection with the temperature control element. The temperature control element is designed for active heating and cooling of the temperature sensor.

The temperature sensor is, according to the invention, in direct contact with the temperature control element.

The thermally conductive body used in the known devices can thereby be omitted. The temperature sensor also itself serves as a thermally conductive body. A miniaturization of the device is therefore possible. The thermal mass of the temperature sensor is, moreover, very small, so that the temperature of the temperature sensor can be changed by a small temperature control element. Since the temperature sensor is arranged directly at the temperature control element, a second temperature sensor also becomes unnecessary, since, due to the arrangement at the temperature control element and the short thermal transfer paths, the temperature of the temperature control element corresponds to the temperature of the temperature sensor. It can be seen that the temperature sensor can only determine the temperature in the process chamber when the temperature control element is not in operation. As soon the temperature control element is operated and heats or cools the temperature sensor, the temperature sensor determines its own temperature.

The device according to the invention is operated as follows: The temperature of the temperature control element is first increased, so that the temperature of the temperature sensor is also increased above the condensation temperature of the gas under the conditions present in the process chamber. It is in this way ensured that the measuring surface of the temperature sensor, which serves simultaneously as the condensation-facilitating surface, is dry. The temperature control element is then cooled, so that condensation is enabled at the measuring surface of the temperature sensor. Condensation heat is released by the condensation of the gas, which affects the rate of cooling of the temperature sensor. This can be seen as a discontinuity (e.g. as a "kink") in a graphic illustration of the temperature curve of the temperature sensor. In the best case an equilibrium develops, so that a plateau phase of the dew point temperature can be recognized in the graphic illustration. The dew point of the gas in the immediate surroundings of the device can thus be measured.

In one preferred form of embodiment the temperature sensor and the temperature control element are electrically insulated from one another.

Such an arrangement is, in particular, necessary when the temperature control element consists of an electrically conductive material, and the temperature sensor also has electrically conductive parts (e.g. wires), that are arranged directly at the temperature control element and could otherwise to a short-circuit or impair the operation of the device. It is obvious that the electrical insulation also enables good heat conduction between the temperature sensor and the temperature control element.

It should be noted here that in the context of the present invention, even though an electrically insulating layer is present between the temperature control element and the temperature sensor, the temperature sensor is nevertheless understood to be in direct contact with the temperature control element, since there is no thermally conductive body (heat pipe) positioned in between them.

The temperature control element is preferably designed as a Peltier element.

Peltier elements are characterized in particular by a very fast response time to a change in temperature, and can also quickly introduce heat into and remove it from a body (in this case the temperature sensor). The Peltier elements can moreover be made very small, so that the device as a whole can have a very small implementation.

The temperature control element is preferably provided with a heatsink.

This allows the heat that is withdrawn therefrom when cooling the temperature sensor to be better dissipated. A heatsink is in particular advantageous in the case of a temperature control element designed as a Peltier element. The heatsink is arranged on that side of the Peltier element that heats up when the temperature sensor is cooled, in order to ensure better cooling of the temperature sensor.

In one preferred form of embodiment, the temperature sensor is designed as a thermocouple. A thermocouple consists essentially of two conductors of different materials that are connected together at one end.

The junction site of a first conductor and of a second conductor of the thermocouple here forms a condensation-facilitating surface. The junction site, which is usually designed as a weld point of the two lines, thus ideally provides the only condensation-facilitating surface of the device which, when the device is under the conditions of intended use, is arranged in the process chamber and is employed for determining the dew point.

The junction site can here also be arranged at the temperature control element or slightly spaced apart from it. It is important for the present invention that the junction site is in operative, thermally conductive connection with the temperature control element, and that the distance between the junction site and the temperature control element is kept as small as possible in order to keep the effects of the thermal conduction low.

Preferably, the thermocouple, with the exception of the junction site of the two conductors, and at least parts of the temperature control element are surrounded by a thermally insulating and gas-tight layer.

In this way it is ensured that an exchange of heat with the surroundings (process chamber) only takes place through the unprotected part of the device (the junction site), so that the measured values are not affected by the heat exchange processes of the rest of the device. In addition, the layer protects the rest of the device from moisture and corrosion. Parts of the temperature control element, in particular when a heatsink is present, are not protected by the layer, in order to permit the greatest possible heat dissipation when the temperature control element is cooling.

Thermosetting plastics, paints, vapor deposits and, particularly preferably, synthetic resins are used as materials for the layer.

As described earlier, the junction site of the two lines of the thermocouple ideally provides the only condensation-facilitating surface of the device. It can, however, be the case that in the transition region to the junction site, the layer is also partially subject to condensation when the device is in operation due to the low thickness of the layer. These side effects can, however, be largely ignored through the precise selection of the material and execution of the layer.

The junction site is preferably coated with a thermally conductive and gas-tight layer.

Such a coating can be used in forms of embodiment with and without a thermally insulating and gas-tight layer, and in particular protects the junction site from corrosion.

In an alternative form of embodiment of the device according to the invention, the temperature sensor is designed as a resistive temperature sensor. The temperature sensor is in particular designed as a platinum measuring resistor, which is particularly preferably vapor-deposited onto the temperature control element.

Such a device is particularly easy to manufacture, and, depending on the intended use, allows the provision of a larger condensation-facilitating surface than in the case of devices with a thermocouple.

This variant is in particular suitable for the determination of the dew point of process chamber volumes which, in comparison to the condensation-facilitating surface, can in effect be considered as infinite.

The temperature sensor is preferably covered by a thermally conductive and gas-tight protective layer which forms a condensation-facilitating surface. The protective layer thus provides the only condensation-facilitating surface of the device which, when the device is under the conditions of intended use, is arranged in the process chamber and is employed for determining the dew point.

The protective layer protects the sensor from moisture and corrosion, and at the same time allows a measurement of the temperature, since the protective layer is designed to be thermally conductive.

The device preferably furthermore comprises a second temperature sensor arranged at the temperature control element for determining the temperature of the temperature control element.

A second temperature measurement is preferably used to reinforce the measurement signal. Instead of the signal at the first temperature sensor (temperature), a difference between the temperature measured by the first temperature sensor, which is affected by the condensation process at the condensation-facilitating surface, and the temperature measured by the second temperature sensor, which essentially corresponds to the temperature of the temperature control element, is used to determine the dew point. When no condensation takes place at the condensation-facilitating surface both temperatures follow similar curves as the temperature sensor cools (the gradient is essentially the same), so that a difference between the two temperatures is largely constant. This changes as soon as the condensation begins to occur at the condensation-facilitating surface, since the second temperature falls more quickly than the first temperature (ideally the first temperature even remains constant). The value of the difference thus increases. The increase in the value of the difference is accordingly used to determine the dew point.

The device further preferably comprises a pressure sensor for determining the pressure in the process chamber.

The pressure in the process chamber is known as a rule. The measured dew point can thus be compared with a reference value from a saturated steam table, in order to establish whether the conditions measured in the process chamber truly correspond to the conditions that are expected and necessary for the sterilization. Through the integration of a pressure sensor, a device can be provided that permits a comprehensive monitoring of the process chamber. The process reliability can be increased through reference to the pressure, since, on the one hand, pressure deviations in the process chamber can be recognized (e.g. in a cavity where the pressure adjusts with a delay in comparison to the rest of the process chamber), and on the other hand a redundancy of pressure sensors is present.

The device further comprises a control and evaluation unit that is designed to determine the dew point temperature on the basis of discontinuities in the temperature curve of the temperature determined by the temperature sensor.

The control and evaluation unit can be designed integrally with the device, or can be in communicative connection with the device itself via a wired or wireless connection. As already explained at the beginning, as the temperature sensor is cooled, preferably at a constant cooling rate, and on reaching the dew point temperature at the condensation-facilitating surface of the temperature sensor, the condensation heat of the gas is released into the process chamber. This leads to a discontinuity in the temperature curve which is reproduced in a graphic illustration as, for example, a "kink" in the cooling curve. The temperature at which the discontinuity occurs is used to determine the dew point temperature in the surroundings of the temperature sensor. The gas is to a greater or lesser extent supercooled, depending on the cooling rate of the temperature sensor, so that the temperature at which the discontinuity occurs does not correspond exactly to the dew point temperature, which means that in some circumstances a correction is necessary, although said correction can be ascertained in a device-specific and method-specific manner.

The invention further relates to a heat treatment device comprising a process chamber which can be supplied with a process gas and at least one device as described above for determining the dew point. The heat treatment device is preferably a sterilization device in which the process chamber is supplied with steam.

Through the integration of a device according to the invention for determining the dew point in a heat treatment device, an increased process reliability can be achieved, wherein the monitoring, effectively in real time, of the dew point for example allows a treatment to be interrupted if the conditions for a successful heat treatment are not satisfied. Savings in costs and energy are thus also possible, since it is not necessary to reach the end of the heat treatment first to establish whether the heat treatment itself was successful.

In conclusion it should also be noted that in the description above the discussion of a process chamber or of the determination of the dew point of a gas in the process chamber is always under discussion. It can, however, be seen that in some circumstances the process chamber in which the dew point is determined (e.g. the interior of an endoscope) is not the same as a total process chamber (e.g. treatment chamber of a sterilizer). Expressed otherwise, the process chamber in which the dew point is determined can be a sub-unit of a larger, second process chamber.

The invention is described better below with reference to preferred exemplary embodiments in connection with the figures. Here:

Figure 1:
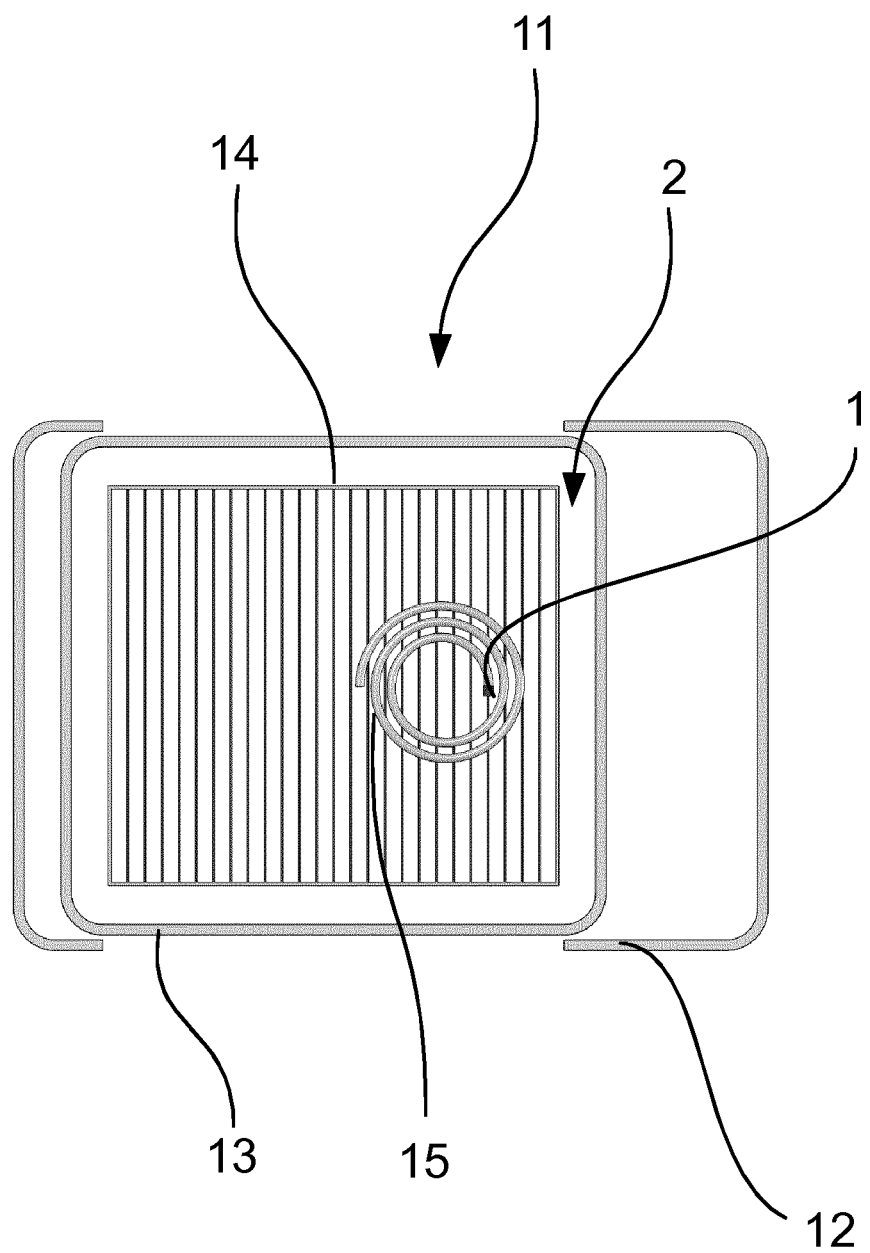
FIG. 1 shows a schematic sectional view of a sterilization device with an object placed therein.

A heat treatment device 11 is illustrated schematically in FIG. 1. The treatment device 11 comprises a housing 12 with a chamber wall 13 that defines a process chamber 2. The process chamber, which is hermetically sealed, is supplied during sterilization with an atmosphere of saturated steam, and is maintained in this state for a specified time until it can be ensured that the eradication of pathogens required for sterilization has taken place.

A load-carrying level 14 in the form of a grille is arranged in the process chamber 2. A rolled-up dummy endoscope 15 is shown schematically on the load-carrying level 14.

An endoscope is usually designed as a hose-like hollow body. For this reason it is not possible to ensure that the same atmosphere of saturated steam has developed in the cavity of the endoscope as in the rest of the process chamber 2. To enable a check of the conditions present in the cavity of the endoscope, a device 1 according to the invention, which is described better below, is therefore arranged.

An endoscope is used in the following description purely as an exemplary object. The device according to the invention is, however, usable wherever the conditions in a partial region of a heat treatment device can deviate from the conditions in the rest of the process chamber 2, as is, for example, the case with stacks of hand towels, capillaries, etc.

It should be noted here that as a rule the device 1 is not arranged at a "real" endoscope, but in a dummy endoscope that has the same properties (diameter, material etc.) as the endoscope 15 to be sterilized, since it is often not possible to connect a device 1 to a "real" endoscope at all. Since it can be assumed that the probability of a deviation from the conditions in the process chamber 2 is highest in the center of a "real" endoscope, the dummy endoscope 15 is implemented with half the length of the "real" endoscope, and with a closed end. The device 1 is arranged at the closed end of the dummy endoscope 15.

It is further to be noted that a process chamber 2 and a cavity of an endoscope are under discussion in the following description. The cavity of the endoscope is part of the process chamber 2. As a result of the properties of the endoscope it can, however, be the case that the same conditions are not present in the cavity of the endoscope and in the rest of the process chamber 2.

Figure 2:
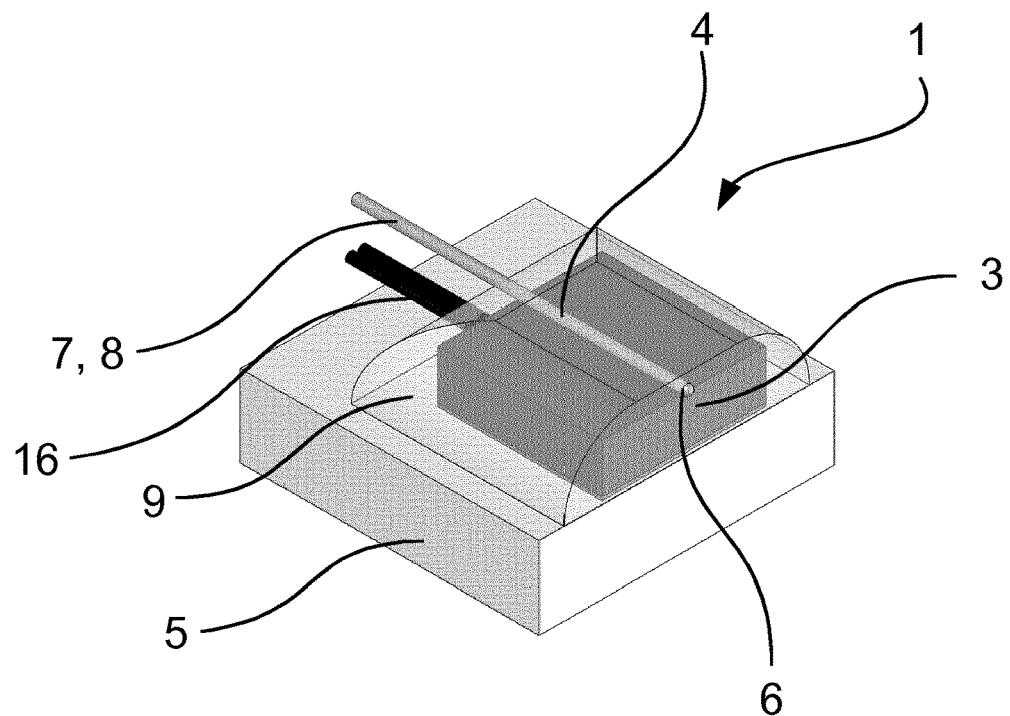
FIG. 2 shows a schematic, perspective view of a first form of embodiment of the device.
Figure 3:
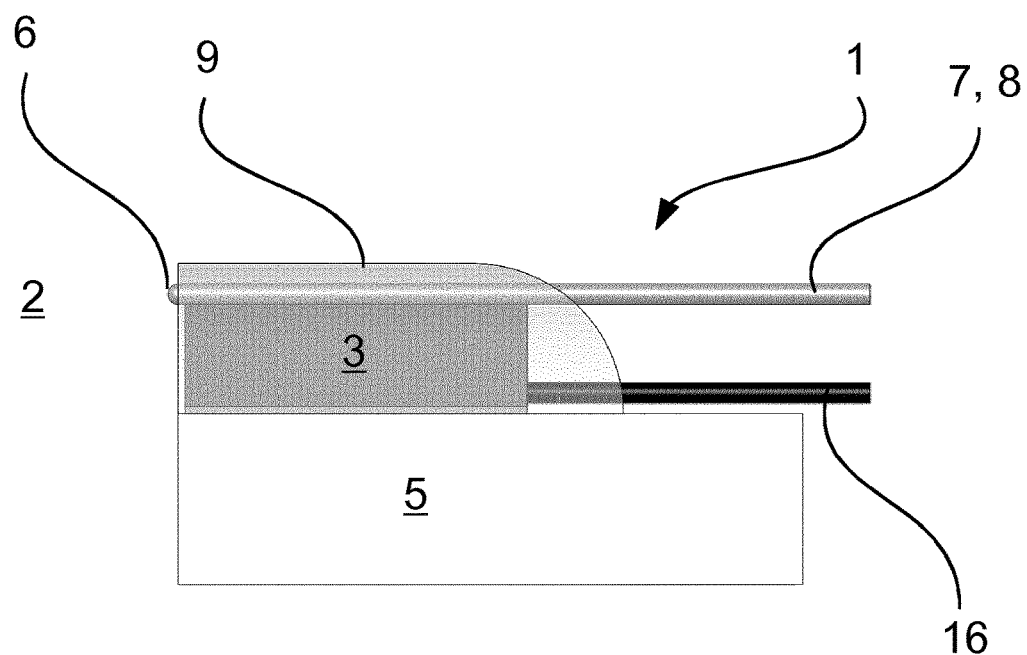
FIG. 3 shows a sectional view through the device of FIG. 2.

A first form of embodiment of the device 1 is shown in FIGS. 2 and 3.

The device 1 comprises a Peltier element 3 which is arranged on an aluminum cooling element 5. The aluminum cooling element 5 can comprise cooling ribs which, for the sake of simplicity however, are not illustrated in FIGS. 2 to 5. A feed 16 for the operation of the Peltier element 3 is also present.

A thermocouple 4 is arranged on the Peltier element 3. The thermocouple 4 comprises two conductors 7 and 8 which are connected together at a junction site 6. As can be seen from FIG. 2, the junction site 6, when under the conditions of intended use, faces the process chamber 2 (or, to be more precise, the cavity of the endoscope 15).

The thermocouple 4 is in operative, thermally conductive connection with the Peltier element 3, although electrically insulated from the latter by means of a layer, not illustrated. The thermocouple 4 can thus be heated and cooled by means of the Peltier element 3.

A synthetic resin mass 9, shown as transparent for the sake of clarity, surrounds the Peltier element 3 and the thermocouple 4, and protects these from moisture and corrosion. At the same time, the synthetic resin mass 9 serves as a thermal insulation for the device 1, so that an exchange of heat with the cavity of the dummy endoscope 15 can only take place through the unprotected regions of the device 1. The cooling element 5 is only partially surrounded by the synthetic resin mass 9, since the heat generated by the Peltier element 3 at the contact surface between the Peltier element 3 and the cooling element 5 when cooling the thermocouple 4 should be dissipated. Further parts of the cooling element 5 can be surrounded by the synthetic resin mass 9, depending on the application. It can, for example, be the case that the cooling element 5 releases the heat into the process chamber 2 outside the cavity of the dummy endoscope 15, in order not to affect the atmosphere in the cavity.

Only the junction site 6 protrudes out of the synthetic resin mass 9 and into the process chamber 2, and thus allows the determination of the dew point, which is described later. It can further be seen that the conductors 7 and 8 of the thermocouple 4, as well as the feed 16 of the Peltier element 3, are also only partially protected by the synthetic resin mass 9. This does not have any effect on the device 1, since the conductors 7 and 8, as well as the feed 16, are also surrounded by an insulation.

To determine the dew point, the thermocouple 4 is first heated with the aid of the Peltier element to a temperature above the dew point of the gas that is in the process chamber 2, in order to ensure that there is no condensed gas on the surface of the junction site 6. The thermocouple 4 is then cooled at a constant cooling rate. On reaching the dew point temperature, condensation of the gas at the surface of the junction site 6 takes place. The condensation heat released as a result affects the cooling of the thermocouple 6, so that a discontinuity arises in the temperature curve. The dew point can thus be determined very easily by determining the discontinuity in the temperature curve.

A device 1 according to the invention can, for example, first be heated for 2 to 5 seconds above the dew point temperature, and then cooled down at a cooling rate of 10 K/s. The dew point can thus be determined in less than 10 seconds. Through repeating the determination of the dew point, this allows a continuous monitoring of the heat treatment that is taking place, so that if the necessary conditions are not satisfied in the cavity, it can be stopped immediately and restarted. The process reliability can be increased in this way, since monitoring of whether the heat treatment was successful can take place effectively in real time.

Figure 4:
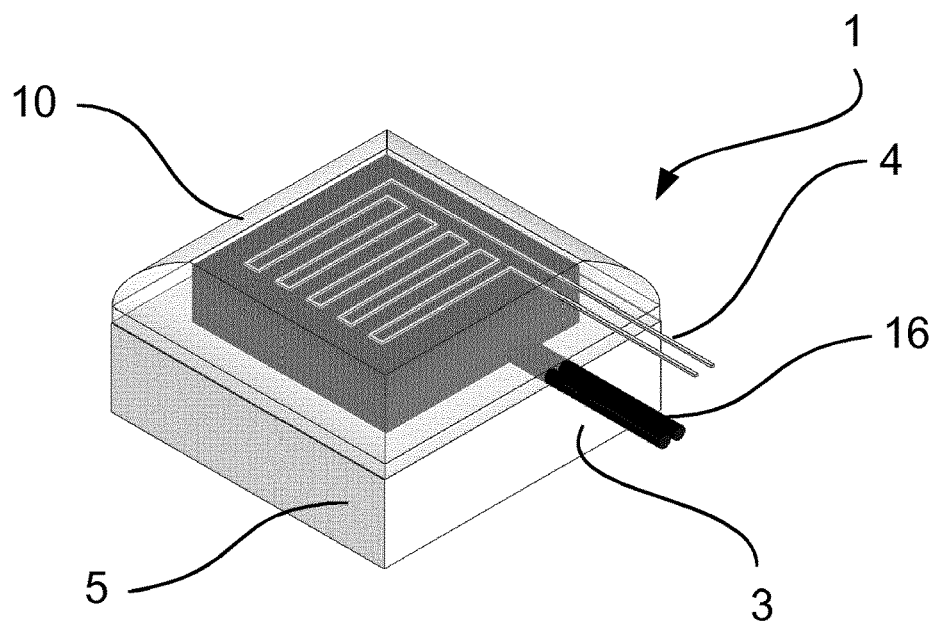
FIG. 4 shows a schematic, perspective view of a second form of embodiment of the device.
Figure 5:
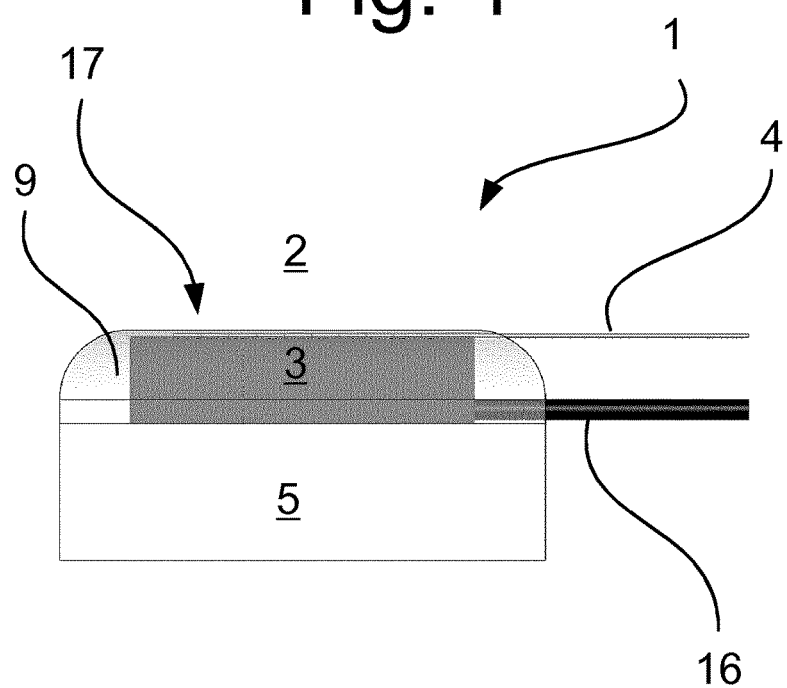
FIG. 5 shows a sectional view through the device of FIG. 4.

A second form of embodiment of the device 1 is shown in FIGS. 4 and 5.

The device 1 comprises a Peltier element 3 which is arranged on an aluminum cooling element 5. A feed 16 for the operation of the Peltier element 3 is also present.

A resistive temperature sensor 4 is arranged on the Peltier element 3. The meandering form of the temperature sensor 4 increases the length of the resistive part of the temperature sensor 4, so that a more precise measurement of the temperature is possible, or more pronounced measured values can be generated. The temperature sensor 4 can, for example, be formed as a vapor-deposited platinum wire.

The temperature sensor 4 is in operative, thermally conductive connection with the Peltier element 3, although electrically insulated from the latter by means of a layer, not illustrated. The temperature sensor 4 can thus be heated and cooled by means of the Peltier element 3.

As can be seen from FIG. 5, the temperature sensor 4 is arranged when under the conditions of intended use on the side of the Peltier element 3 that faces the process chamber 2 (or, to be more precise, the cavity of the dummy endoscope 15).

A protective layer 10, shown as transparent for the sake of clarity, surrounds the Peltier element 3, and protects it from moisture and corrosion. The protective layer 10 serves at the same time as a thermal insulation for the device 1, so that an exchange of heat with the process chamber 2 can only take place via the region 17 in which the temperature sensor 4 is exposed.

The cooling element 5 is furthermore only partially surrounded by the protective layer 10, since the heat generated by the Peltier element 3 at the contact surface between the Peltier element 3 and the cooling element 5 when cooling the temperature sensor 4 should be dissipated. Further parts of the cooling element 5 can be surrounded by the protective layer 10, depending on the application. It can, for example, be the case that the cooling element 5 releases the heat into the process chamber 2 but outside the cavity of the dummy endoscope 15, in order not to affect the atmosphere in the cavity.

The measurement of the dew point takes place similarly to the measurement with a device 1 according to FIGS. 2 and 3, with the difference that the condensation-facilitating surface is the surface of the temperature sensor 4. This condensation-facilitating surface is first heated and then cooled until the condensation of the gas begins. In this case too, the condensation heat released has the effect that a discontinuity occurs in the temperature curve as the condensation-facilitating surface is cooled.

The invention claimed is:

1. A device for measuring a dew point of a gas in a process chamber comprising:
    a temperature control element, and
    a temperature sensor for determining the temperature in the process chamber,
    wherein the temperature sensor is in operative, thermally conductive connection with the temperature control element,
    wherein the temperature control element is designed for active heating and cooling of the temperature sensor, and
    the temperature sensor is in direct contact with the temperature control element, and wherein the temperature sensor is a thermocouple, wherein the device is designed to determine the dew point of the gas in the process chamber by dewing the junction site of a first conductor and of a second conductor of the thermocouple as the only dewable surface of the device.

2. The device as claimed in claim 1, wherein the temperature sensor and the temperature control element are electrically insulated from one another.

3. The device as claimed in claim 1, wherein the temperature control element is a Peltier element.

4. The device as claimed in claim 1, wherein the temperature control element is provided with a heatsink.

5. The device as claimed in claim 1, wherein a thermally insulating and gas-tight layer surrounds the thermocouple, with the exception of the junction site of the two conductors.

6. The device as claimed in claim 1, wherein the junction site is covered with a thermally conductive and gas-tight layer.

7. The device as claimed in claim 1, wherein the device furthermore comprises a second temperature sensor arranged at the temperature control element for determining the temperature of the temperature control element.

8. The device as claimed in claim 1, wherein the device furthermore comprises a pressure sensor for determining the pressure in the process chamber.

9. The device as claimed in claim 1, wherein the device further comprises a control and evaluation unit that is designed to determine a dew point temperature on a basis of discontinuities in a temperature curve of the temperature determined by the temperature sensor.

10. A heat treatment device comprising a process chamber which can be supplied with a process gas, and at least one device for measuring the dew point as claimed in claim 1.

\* \* \* \* \*